United States Patent [19]
Ross et al.

[11] Patent Number: 6,156,744
[45] Date of Patent: Dec. 5, 2000

[54] DT-DIAPHORASE DIRECTED ANTI-TUMOR AGENTS

[75] Inventors: David Ross, Boulder, Colo.; John Butler, Stockport; Robert H. J. Hargreaves, Bury, both of United Kingdom; David Siegel, Denver, Colo.; Howard D. Beall, Missoula, Mont.

[73] Assignees: Cancer Research Campaign Tech (London); University Technology Corp.; University of Salford, both of Boulder, Colo.

[21] Appl. No.: 09/317,906

[22] Filed: May 24, 1999

Related U.S. Application Data

[63] Continuation-in-part of application No. 09/044,453, Mar. 19, 1998, abandoned.

[51] Int. Cl.$^7$ ..................... A61K 31/396; C07D 403/02; C07D 403/08
[52] U.S. Cl. ............................. 514/183; 548/963
[58] Field of Search ............................. 548/963; 514/183

[56] References Cited

PUBLICATIONS

Winski et al.; Dec. 1998, "A New Screening System for NAD(P)H: Quinone Oxidoreductase (NQO1)–directed Antitumor Quinones: Identification of a New Aziridinylbenzoquinone, RH1, as a NQO1–directed Antitumor Agent" Clincal Cancer Research, 4:3083–3088.
Smitskamp–Wilms, E. et al; DT–diaphorase activity in normal and neoplastic human tissues; an indicator for sensitivity to bioreductive agents; Br.J. Cancer, 72:917–921,(1995).
Gibson, N.W., et al; Relationship between DT–diaphorase mediated metabolism of a series of aziridinylbenzoquinones and DNA damage and cytotoxicity; Mol. Pharmacol., 42:531–536, (1992).
Lee, C.–S., et al; Alteration in DNA cross–linking and sequenec selectivity of a series of aziridinylbenzoquinones after enzymatic reduction by DT–diaphorase; Biochemistry, 31:3019–3025, (1992).
Fitzsimmons, S.A., et al; Reductase enzyme expression ascross the National Cancer Institute tumor cell line panel: Correlation with sensitivity to mitomycin C and EO9; JNCI, 88:259–269, (1996).
Phillips, R.M., et al; Increased activity and expression of NAD(P)H:quinone acceptor oxidoreductase in confluent cell cultures and within multicellular spheroids. Cancer Res., 54:3766–3771, (1994).
Traver, R.D., et al, Characterization of a polymorphism in NAD(P)H: Quinone oxidoreductase (DT–diaphorase), Br. J. Cancer, 75:69–75, 1997).
Gustafson, D. L., et al, Expression of human NQO1 (DT–diaphorase) in chinese hamster ovary cells: Effects on the toxicity of antitumor quinones; Mol. Pharmacol., 502:728–735, (1996).

Cummings, J., et al, Antitumor Activity of the Novel Bioreductive MeDZQ Against Human Non–Small Cell Lung Cancer Xenorgrafts; submitted to the 9th NCI–EORTC Symposium on New Drugs in Cancer Therapy, Amsterdam, The Netherlands, (Mar., 1996).
Beall, H.D., et al, Nicotinamide adenine dinucleotide (phosphate):quinone oxidoreductase (DT–diaphorase) as a target for bioreductive antitumor quinones: Quinone cytotoxicity and selectivity in human lung and breast cancer cell lines, Mol.Pharmacol., 48:499–504, (1995).
Ross, D. et al, DT–diaphorase in activation and detoxification of quinones, Cancer and Metastasis Reviews, 12:83–101, (1993).
Schlager, J., et al., Cytosolic NAD(P)H:(Quinone–Acceptor)Oxidoreductase in Human Normal and Tumor Tissue: Effects of Cigarette Smoking and Alcohol, Int. J. Cancer, 45: 403–409, (1990).
Berger, M., et al., Use of Quinones in Brain Tumor Therapy: Preliminary Results of Preclinical Laboratory Investigations, J. of Toxicology and Environmental Health, 16:713–719, (1985).
Xu, B.H., et al, Mechanism of differential sensitivity of human bladder cancer cells to mitomycin C and its analogue, British J.of Cancer, 69:242–246, (1994).
Malkinson, A., et al, Elevated DT–diaphorase Activity and Messenger RNA Content in Human Non–Small Lung Carcinoma: Relationship to the Response of Lung Tumor Xenografts to Mitomycin C, Cancer Research, 52: 4752–4757 (1992).
Spain, R., The Case for Mitomycin in Non–Small Cell Lung Cancer, Oncology (1993); 50:(suppl 1):35–52.
Beall, H. et al., Metabolism of Bioreductive Antitumor Compounds by Purified Rat and Human DT–Diaphorases, Cancer Research, 54:3196–3201, (1994).
Siegel, D., et al, pH Dependent Inactivation of DT–Diaphorase by Mitomycin C and Porfiromycin, Molecular Pharmacology, 44:1128–1134, (1993).
Ross, D., et al., Bioactivation of Quinones by DT–diaphorase, Molecular, Biochemical, and Chemical Studies; Oncology Research, vol. 6, Nos. 10/11: 493–500, (1994).
Kepa, J.K., et al., Comparison of human NQ01 promoter activity in NSCLC and SCLC cell lines. Proc. Am. Assoc. Cancer Res., 38:2515, (1997). Abstract.
Kelsey, K.T., et al, Ethnic variation in the prevalence of a common NAD(P)H quinone oxidoreductace polymorphism and its implications for anti–cancer chemotherapy, British J. of Cancer, 76(7): 852–854, (1997).

*Primary Examiner*—Laura L. Stockton
*Attorney, Agent, or Firm*—Sheridan Ross P.C.

[57] ABSTRACT

The present invention relates to a novel benzoquinone, 2,5-diaziridinyl-3-(hydroxymethyl)-6-methyl-1,4-benzoquinone and its esters. The compounds can be used to treat tumors exhibiting elevated levels of the enzyme DT-diaphorase.

13 Claims, 6 Drawing Sheets

Time (Days)
RH1 (0.5 mg/kg)

FIG. 5

MeDZQ
(NSC 646714)

DT-DIAPHORASE DIRECTED ANTI-TUMOR AGENTS

CROSS REFERENCE TO RELATED APPLICATIONS

This is a continuation-in part of U.S. Ser. No. 09/044,453, filed on Mar. 19, 1998, which is incorporated by reference in its entirety.

This invention was supported in part by the National Cancer Institute (Grant HHS CA51210). Therefore, the government may have certain rights in the invention.

FIELD OF THE INVENTION

The invention generally relates to novel anti-tumor compounds and, more particularly, to a water-soluble aziridinyl-benzoquinone and its esters.

BACKGROUND OF THE INVENTION

DT-diaphorase (DTD) is an enzyme that is overexpressed in certain cancerous tissues, including breast, colon, liver, bladder, stomach, the central nervous system (CNS) and lung tumors and in melanomas. For example, the expression of DTD is increased up to 80-fold in primary non-small cell lung cancer (NSCLC) relative to normal lung and up to 400-fold in NSCLC relative to small cell lung cancer (SCLC) cell lines [Malkinson et al., Cancer Res., 52:4752–4757 (1992)]. Evidence to date suggests increased expression of DTD reflects increased activity of AP-1 binding proteins that positively regulate DTD transcription [Kepa et al., Cancer Res. 38:2515 (1997)].

Accordingly, it would be desirable to use a DTD-directed approach for cancer therapy. Ideally, the mechanism of action would involve the production of a reactive quinone pro-drug after being reduced by DTD. The reduced quinone pro-drug can then crosslink DNA, which leads to cell death.

Various quinone pro-drugs have been studied to determine their effect on cancer cells expressing DTD. For example, NSCLC xenografts with high DTD activity were more susceptible to the quinone pro-drug mitomycin C than SCLC xenografts with low DTD activity. Although mitomycin C has been shown to have activity in NSCLC, it has two major drawbacks as a useful therapeutic agent in a DTD-directed approach. First, mitomycin C is a very poor substrate for DTD [Beall et al., Cancer Res. 54:3196–3201 (1994)]. Second, metabolism of mitomycin C by DTD is pH-dependent leading to pH-dependent inhibition of DTD at higher pHs [Siegel et al., Mol. Pharmacol., 44:1128–1134 (1993)].

Another quinone pro-drug, E09, is efficiently reduced by DTD, but primarily generates reactive oxygen radicals rather than DNA crosslinks. E09 has been shown to exclusively form DNA strand breaks. Being a conventional "hypoxic-targeting" agent, E09 was not active in spheroid studies demonstrating increased expression of DTD towards the necrotic center of the spheroid. The results probably relate to the poor ability of E09 to penetrate cells and cross cellular membranes [Bibby et al., Int. J. Oncol., 3:661–666 (1993)]. Other conventional "hypoxic-targeting" agents include tirapazamine and the nitroimidazole compounds.

Diaziquone (AZQ) is also an extremely poor substrate for DTD and does not readily form DNA crosslinks after reduction by DTD as reported by Siegel et al., Cancer Res., 50:7293–7300 (1990). In fact, AZQ failed to show any selectivity for DTD-rich cell lines.

MeDZQ (2,5-diaziridinyl-3,6-dimethyl-1,4-benzoquinone) was a promising agent that utilizes the DTD enzyme-directed approach to cancer treatment. MeDZQ: (i) is greater than 150 fold more effective as a substrate for recombinant human DTD than mitomycin C, and (ii) shows pH-independent metabolism and does not inactivate DTD at higher pHs [Beall et al., supra; Ross et al. Oncol. Res., 6:493–500 (1994)]. DNA crosslinking by MeDZQ showed an absolute requirement for reduction of the drug and sequence-selectivity studies demonstrated that the drug crosslinked DNA at GNC sequences [Lee et al., Biochemistry, 31:3019–3025 (1992)]. In addition, there was good correlation between the levels of DTD in NSCLC and breast cancer cell lines and the cytotoxicity of MeDZQ [Beall et al., Mol. Pharmacol. 48:499–504 (1995)]. In fact, recent data from the NCI tumor cell line panel/COMPARE analysis has shown that there is a good correlation between DTD activity and MeDZQ cytotoxicity across 69 human tumor cell lines (r=0.3033, p<0.016).

Although MeDZQ undergoes bioreductive activation, it was designed to be bioactivated specifically by DTD. As such, it is distinctly different from E09, tirapazamine and the nitroimidazole compounds. Unlike these "hypoxic-targeting" compounds, MeDZQ only produces a very modest increase in cytotoxicity under hypoxic conditions relative to aerobic conditions.

CHO cell lines stably transfected with human DTD were produced as reported in Gustafson et al., Mol. Pharmacol., 50:728–735 (1996). The parent non-transfected cell lines had no detectable DTD activity, while the activity of the transfectants ranged from 19–3527 nmol/min/mg protein. The cytotoxicity of MeDZQ was markedly increased as a result of transfecting DTD into CHO cells. Studies in NSCLC xenografts confirmed the relationship between the levels of reducing enzymes and the efficacy of MeDZQ.

The formulation of MeDZQ as a useful therapeutic, however, was hampered by its poor solubility. Therefore, a need exists for anti-cancer agents that have the desirable properties of MeDZQ, but without its poor solubility. The present invention satisfies this need and provides related advantages as well.

SUMMARY OF THE INVENTION

Figure 6:
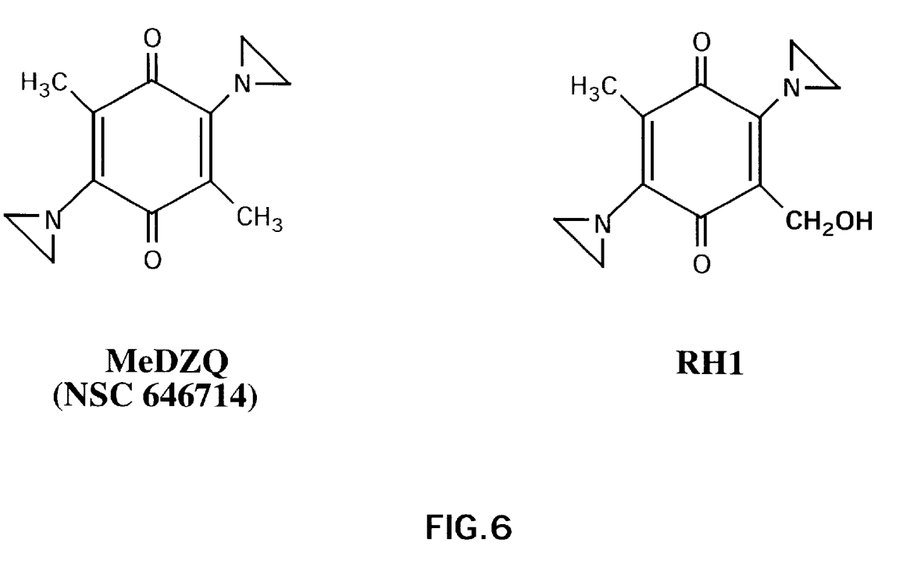
FIG. 6 shows the chemical structure of RH1 and MeDZQ.

The invention generally relates to a novel benzoquinone, 2,5-diaziridinyl-3-(hydroxymethyl)-6-methyl-1,4-benzoquinone, referred to as "RH1" and its esters. The chemical structure of RH1 is shown in FIG. 6, while the general chemical structure of its esters can be depicted as:

wherein R is preferably benzoyl, acetyl, naphthoyl or protected amino acids.

The invention further provides methods of treating a tumor exhibiting elevated DTD activity by administering an effective amount of RH1 or its esters to a patient having such a tumor. Preferably, the methods are used to treat breast, colon, liver, CNS and lung tumors and melanomas. For example, DTD expression is particularly high in non-small cell lung cancers (NSCLC) compared to small cell lung cancer (SCLC). Therefore, RH1 or its esters would be particularly useful for treating NSCLC.

DETAILED DESCRIPTION OF THE INVENTION

The present invention relates to a novel benzoquinone, 2,5-diaziridinyl-3-(hydroxymethyl)-6-methyl-1,4-benzoquinone referred to as RH1. The empirical formula of RH1 is $C_{12}H_{14}N_2O_3$, while the chemical structure of RH1 is shown in FIG. 6 and below:

Similar to MeDZQ, RH1 is bioactivated (i.e., reduced) by DTD and selectively kills cells rich in DTD by crosslinking DNA. Notably, however, RH1 has a different crosslinking specificity relative to MeDZQ. RH1 crosslinks DNA at GCC sequences, whereas MeDZQ crosslinks at GNC sequences.

Figure 1:
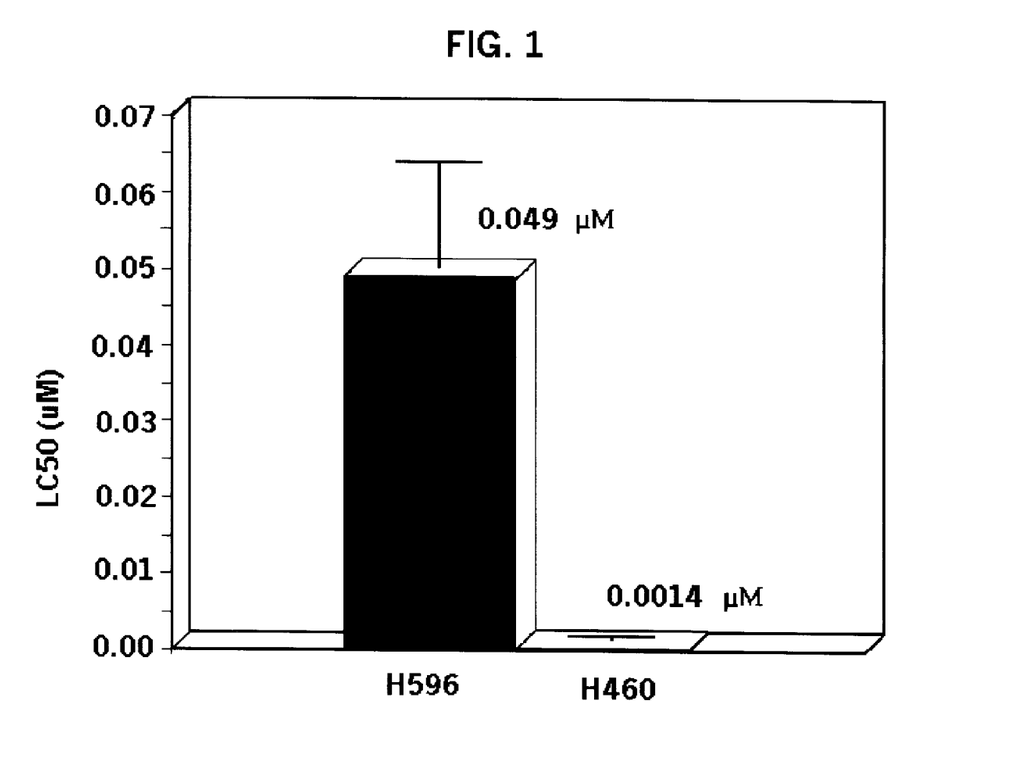
FIG. 1 graphically shows the cytotoxicity of RH1 to human non-small cell lung cancer cell lines (H596 and H460).

RH1 was synthesized in an attempt to overcome the poor solubility of MeDZQ. Surprisingly, the water-soluble RH1 is more effective as a substrate for DT-diaphorase than MeDZQ as shown in Example 2. RH1 is also more cytotoxic to tumor cell lines with elevated DTD activity. FIG. 1 compares the cytotoxicity of RH1 in human non small cell lung tumor cell lines with elevated DTD activity (H460) and those with no detectable DTD activity (H596). RH1 was 350 fold more toxic to tumor cells with elevated DTD activity than to DTD null cells. In comparison to RH1, MeDZQ was less cytotoxic to both H596 and H460 cells and demonstrated less selective toxicity with only a 17 fold differential toxicity to H460 cells containing elevated DTD activity as reported in Ross et al., *Cancer Metastasis Rev.*, 12:83–101 (1993).

Increased cytotoxicity was also observed (FIG. 2) when a human colon tumor cell line with no DTD activity (BE) was compared to a non small cell lung cancer cell line with elevated activity (H460). The cell line BE is a human colon carcinoma that is described in Day et al., *Carcinogenesis* 1:21–32 (1980). The ratio of cytotoxicities of $IC_{50}$ in the cell line containing no DTD activity (BE) to the cell line with elevated DTD activity (H460) was 33 for MeDZQ and 51 for RH1. Similarly, chinese hamster ovary cells (CHO cells) transfected with DTD cDNA resulting in overexpression of DTD (CHO-812) were more susceptible to RH1 -induced cell killing (FIG. 3) relative to the parent cell line (CHO-glyA).

Similar to MeDZQ, RH1 is not a conventional "hypoxic-targeting" approach to chemotherapy. Although MeDZQ and RH1 undergo bioreductive activation similar to other hypoxic-targeting" agents, MeDZQ and RH1 are designed to be bioactivated by DTD processing. Unlike conventional hypoxic-targeting agents, MeDZQ only produces a very modest increase in cytotoxicity under hypoxic conditions relative to aerobic conditions. The reactive hydroquinone metabolite of MeDZQ has appreciable stability (Beall et al., (1994) supra.; Beall et al. (1995) supra.) and similar behavior was observed with RH1.

There is evidence, however, that the cytotoxicity of MeDZQ and RH1 may be increased in hypoxic regions of tumors. This evidence is derived from spheroid studies demonstrating increased expression of DTD towards the necrotic center of the spheroid. The increase in DTD levels correlated with an increased cytotoxicity of MeDZQ to cells in that region of the spheroid as reported in Phillips et al., *Cancer Res.*, 57:3766–3771 (1994).

The invention further relates to the discovery that RH1 pro-drug can be produced in the form of esters encompassed by the following general structure:

The synthesis of the esters involve the general esterification of RH1 acid and 1,3-dicyclihexylcarbodiimide and 4-dimethylaminopyridine. In this manner several analogues can be made. Preferably, R is benzoyl, acetyl, naphthoyl or a protected amino acid. These esters can be cleaved by the action of cellular esterases to produce RH1. The advantages of these esters are that they can be readily synthesized and have different hydrophilic/hydrophobic properties compared to RH1. The in vitro cytotoxicities of these esters are of similar magnitude to those of RH1, but the DTD selectivity is markedly different.

The invention further provides methods of treating a patient having a tumor with elevated DTD activity by administering an effective amount of RH1 or its esters to reduce or otherwise inhibit the growth of such tumors. The anti-tumor agents can be formulated in any pharmaceutically acceptable formulation. Such formulations include liquids, powders, creams, emulsions, pills, troches, suppositories, suspensions, solutions, and the like. Other excipients can also be added and are readily identified by those skilled in the art. Preferably, the anti-tumor agents are soluble in aqueous solutions, are stable, and can be prepared in gram quantities.

Therapeutically effective amounts of the anti-tumor agents can be any amount or doses sufficient to bring about the desired anti-tumor effect and depend, in part, on the condition, type and location of the cancer, the size and condition of the patient, as well as other factors readily known to those skilled in the art. The dosages can be given as a single dose, or as several doses, for example, divided over the course of several weeks.

The anti-tumor agents of the instant invention can be administered by any suitable means, including, for example, orally or by injection. In the preferred embodiment of the invention, the agent is administered by injection. Such injection can be locally administered to any affected area.

A polymorphism in DTD that results in extremely limited amounts or a total lack of the enzyme can be used to screen potential patients. This DTD polymorphism is described in Kelsey et al., Br. J. Cancer, 76:852–854 (1997) and can be readily detected by analyzing the genomic DNA of a potential recipient's blood sample to detect the polymorphism. For example, PCR-RFLP analysis can be used and is well known to those skilled in the art. In African-Americans and Caucasians the prevalence of this polymorphism is 7% and 5%, respectively, while in Hispanics the prevalence is 16% and in Asian populations the prevalence is 22%.

Thus, individuals can be pre-screened for the polymorphism. Individuals carrying the polymorphism would have no detectable levels of DT-diaphorase and would, therefore, not benefit from the compounds of the present invention. Such screening would be useful, for example, to exclude subjects from a clinical study.

The following Examples are intended to illustrate, without limiting, the invention.

EXAMPLE 1

Chemical Synthesis of RH1

To a stirred solution of 2-hydroxymethyl-5-methyl-1,4-benzoquinone (10 g, 65.8 mmol) in ethanol (250 ml), under $N_2$ at 0° C., was added aziridine (6.8 ml, 5.66 g, 131.6 mmol). After 20 mins the solution was allowed to rise room temperature and stirred for a further 5 hours. The solvent was then reduced in vacuo to approximately 100 mls and then cooled on ice. The resulting precipitate was filtered and washed with ice cold ethanol (50 ml). A further crop could be obtained by reducing the solvent to ~50 ml, cooling and filtering again. The combined yield was 2.813 g of dark red crystals. (18.3%, m.p. 178–9° C.); $^1$H NMR (200 MHz, $CDCl_3$): δ 4.56 (2H, d, J=6 Hz, $CH_2$), 2.64 (1H, t, J=6 Hz, OH), 2.38 (4H, s, Az), 2.28 (4H, s, Az), 2.0 (3H, s, $CH_3$); MS El m/z: 234 ($M^+$), 219, 191, 177, 163, 149; $v_{max}$ (KBr disc): 3483, 2995, 1637, 1585, 1383, 1300, 1159; HREIMS. Found 234.1005 $C_{12}H_{14}N_2O_3$ requires 234.1004.

RH1 is easily synthesized with very high purity (>99%). RH1 is readily soluble in aqueous solution (solubility in phosphate buffered saline is>0.5mg/ml at 25° C.). The RH1 solutions are very stable with a half life of RH1 in phosphate buffer (0.1 M, pH=7) of more than 2 days at 25° C. The free hydroxyl group of RH1 accounts for its water solubility that leads to a shorter half-life in pharmacokinetics.

EXAMPLE 2

MeDZQ and RH1 as DT-Diphorase Substrates

The relative abilities of MeDZQ and RH1 to serve as substrates for human recombinant DT-diaphorase were determined. Both quinones (0.05 mM) were incubated with 10–100 ng/ml recombinant human DT-diaphorase and NADH (0.2 mM) in 25 mM Tris buffer, pH 7.4, containing 1 mM DETAPAC. NADH removal was measured by HPLC as described in Beall et al., (1995), supra. The results are shown in Table 1 (n=3).

TABLE 1

| | Quinone Removal | NADH Removal |
|---|---|---|
| MeDZQ | 9.7 ± 2.2 | 21.6 ± 4.0 |
| RH1 | 28.2 ± 4.2 | 45.2 ± 6.3 |

EXAMPLE 3

Cytotoxicity of RH1 in NSCLC

Studies were conducted to determine the cytotoxicity of RH1 against human non small cell lung cancer cell lines. H596 cells are DT-diaphorase null due to a mutation in the DT-diaphorase gene, while H460 cells have elevated DT-diaphorase levels as described in Beall et al., (1995) supra and Traver et al., Br. J. Cancer, 75:69–75 (1997). The cell lines H460 and H596 are available from the American Tissue Type Culture Collection (ATCC), Rockville, Md. Cytotoxicity was determined after a 2 hour drug exposure in serumless medium using the MTT assay as described in detail in Beall et al., (1995), supra. The results are shown in FIG. 1.

EXAMPLE 4

Cytotoxicity of RH1 and MeDZQ

Figure 2:
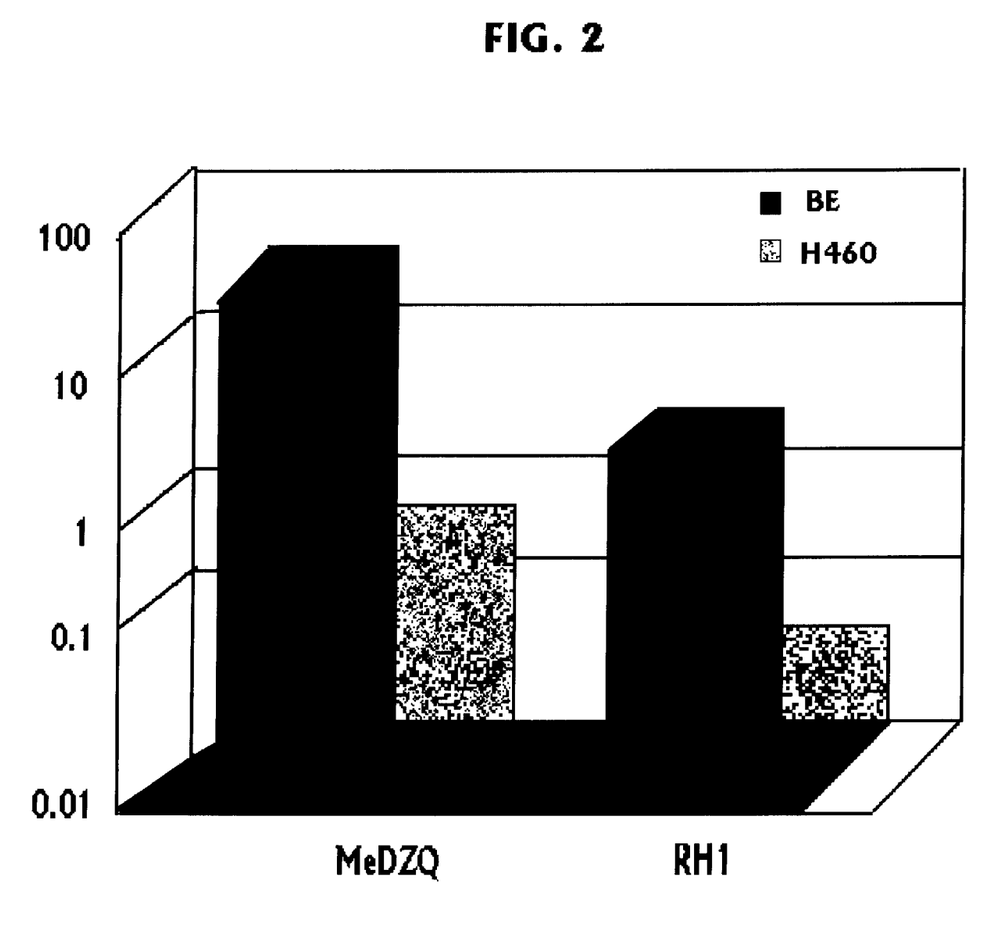
FIG. 2 shows the results of cytotoxicity studies of RH1 and MeDZQ to BE human colon carcinoma cells and H460 human non-small cell lung cancer cells.

The cytotoxicity of RH1 and MeDZQ to BE human colon carcinoma cells and H460 human non small cell lung cancer cells was determined. BE cells are DT-diaphorase null due to a mutation in the DT-diaphorase gene, while H460 cells have elevated DT-diaphorase levels (Traver et al., (1997) supra.). Cytotoxicity was determined using the MTT assay and cells were exposed to drug continuously throughout the four day assay. The results are shown in FIG. 2.

EXAMPLE 5

Cytotoxicity of RH1

Figure 3:
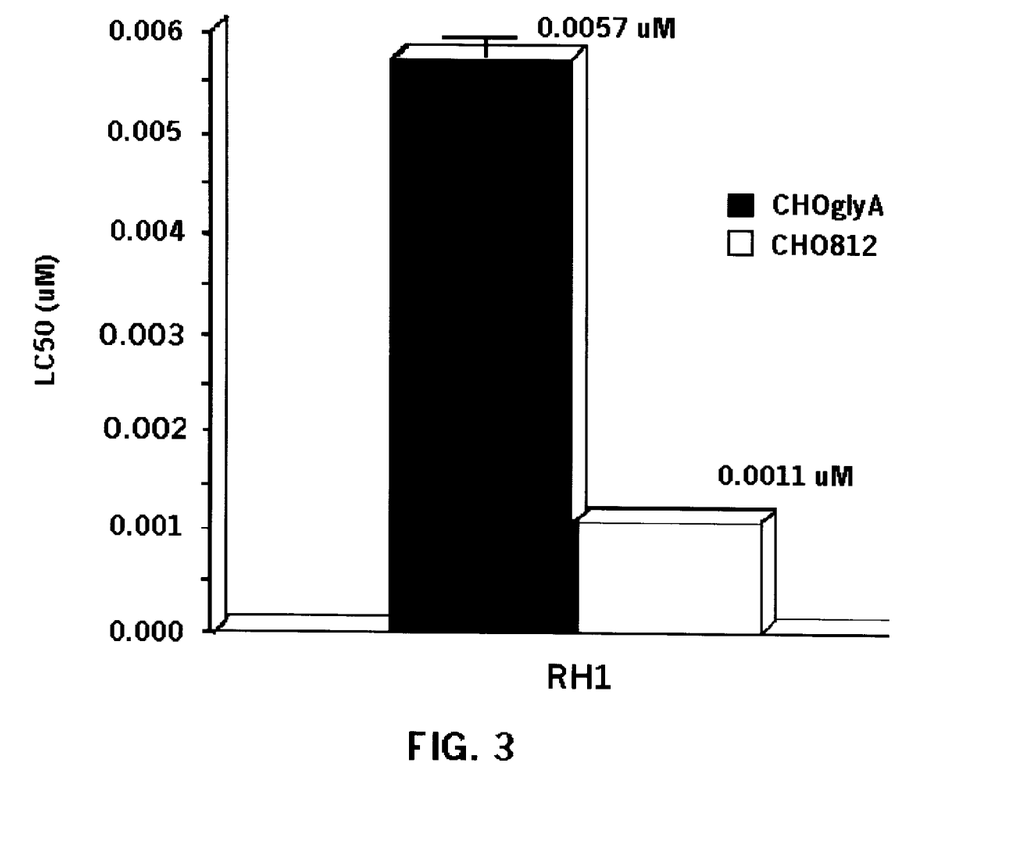
FIG. 3 shows the cytotoxicity of RH1 to CHOgly A and CH0812 cells.

Further studies were conducted to determine the cytotoxicity of RH1 to CHOglyA and CHO812 cells. CHOglyA cells have non detectable levels of DT-diaphorase, whereas CHO812 cells have elevated levels of DT-diaphorase as reported in Gustafson et al., (1996) supra. The original CHO cell lines were obtained from the American Type Culture Collection, Rockville, Md. The results of these studies are shown in FIG. 3. The results show that chinese hamster ovary cells transfected with DT-diaphorase cDNA resulted in overexpression of DT-diaphorase (CHO-812) were more susceptible to RH1-induced cell killing relative to the parent cell line (CHOglyA).

Figure 4:
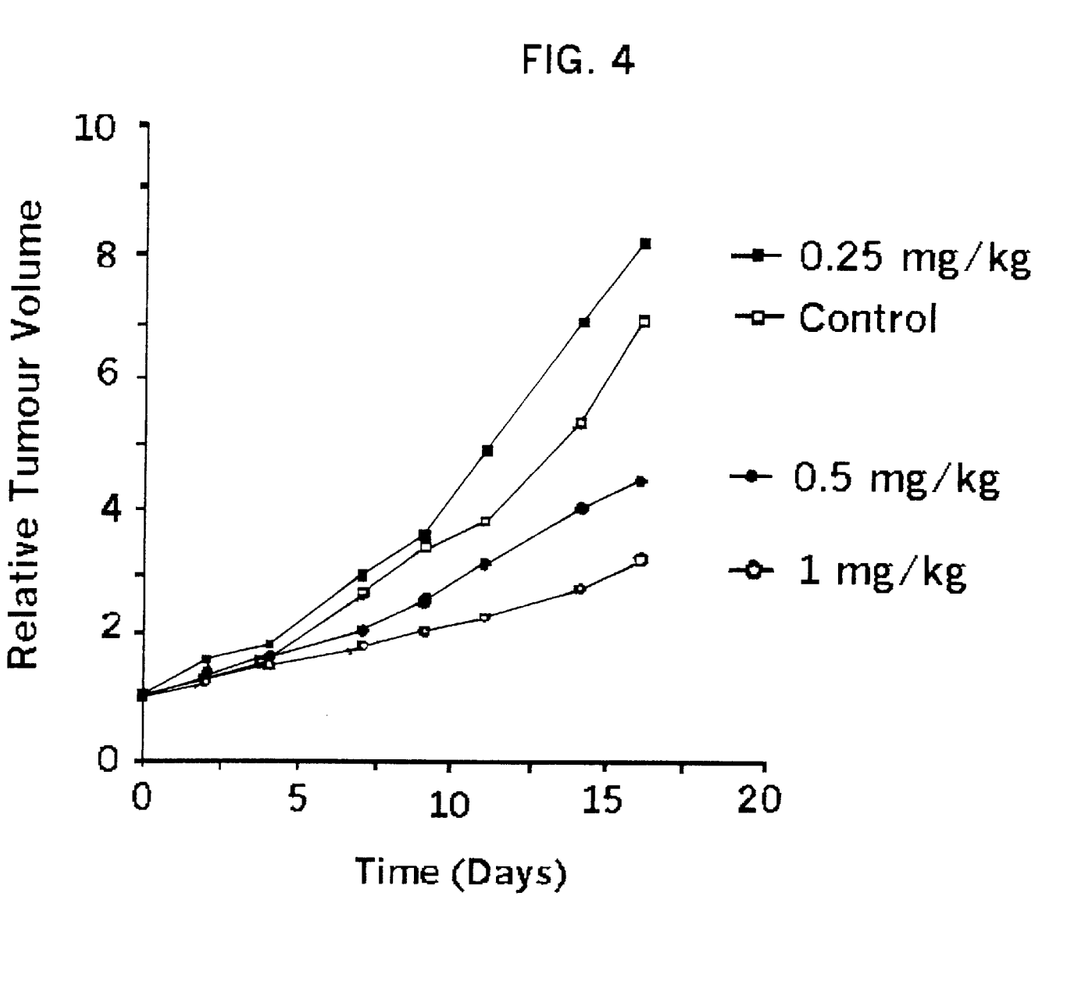
FIG. 4 shows the antitumor activity of RH1 against a non small cell lung cancer xenograft (NX002).

The anti-tumor activity of RH1 was also determined against a non small cell lung cancer xenograft designated as NX002. The results are shown in FIG. 4.

Figure 5:
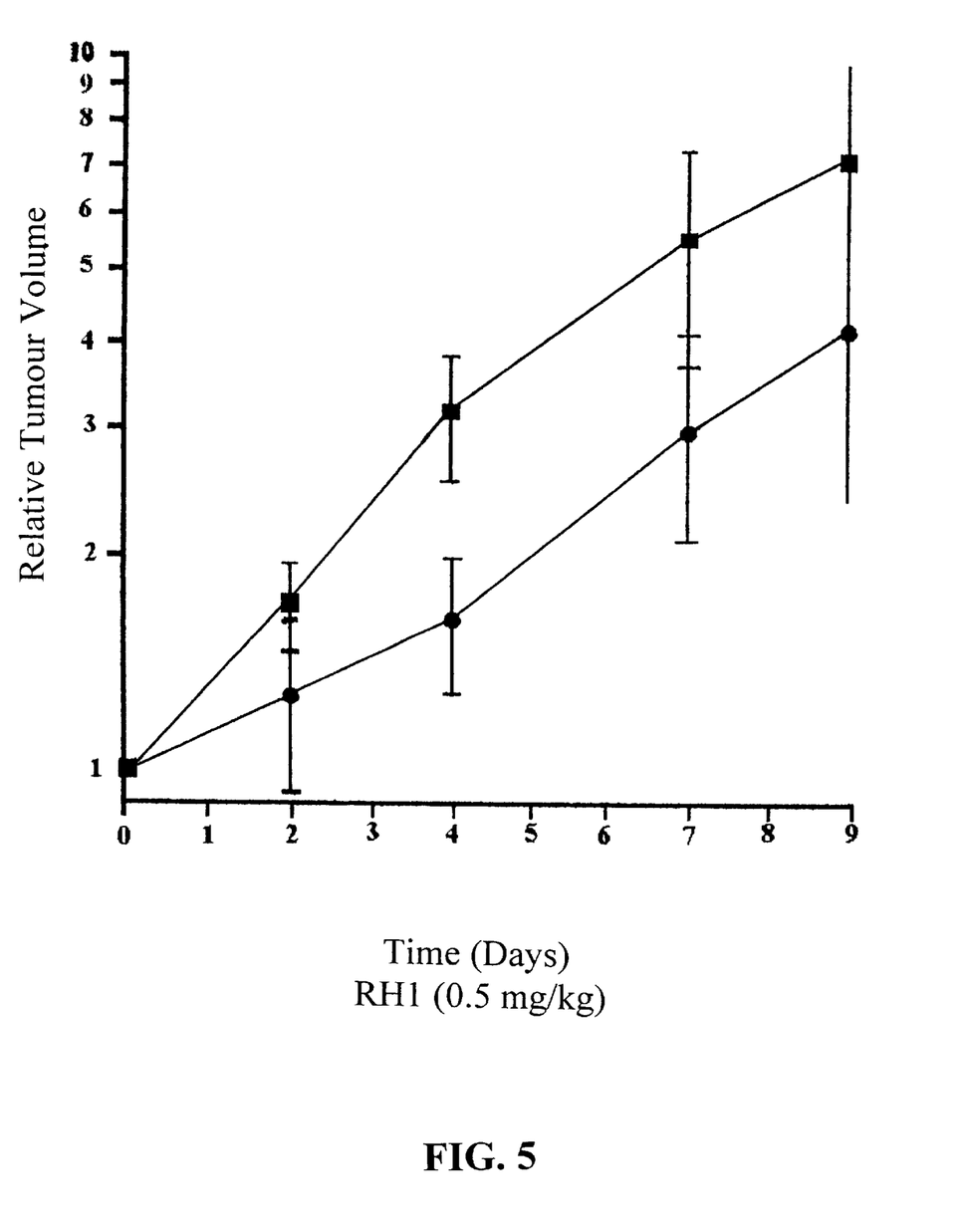
FIG. 5 shows antitumor activity of RH1 against non small cell lung cancer xenograft (H460).

The anti-tumor activity of RH1 was further tested against a non small cell lung cancer xenograft (H460), with the results shown in FIG. 5.

EXAMPLE 6

Benzoyl RH1

The benzoyl ester of RH1 (3,6-diaziridinyl-5-methyl-1,4-benzoquinone) was synthesized. A solution of RH1 (50 mg, 0.21 mmol), benzoic acid (30 mg, 0.24 mmol), DCC (60 mg, 0.29 mmol) and DMAP (10 mg, 0.08 mmol) in DCM (10 ml)

was stirred for 24 hrs. T.l.c. showed that all the RH1 had reacted and the solvent was removed in vacuo. The residue was then passed down a silica column using petroleum ether 40:60/ethyl acetate (3:1→2:1) as the eluent to yield a red solid. (51 mg, 71%, m.p. 149–50° C.); $^1$H NMR (300 MHz, CDCl$_3$): δ 8.02 (2H, m, Ar—H 2 and 6), 7.57 (1H, m, Ar—H 4), 7.43 (2H, m, Ar—H 3 and 5), 5.33 (2H, s, CH$_2$), 2.44 (4H, s, Az), 2.35 (4H, s, Az), 2.07 (3H, s, CH$_3$); MS (EI+) m/z: 338 (M$^+$), 233, 218, 122, 105; $v_{max}$ (film): 1716, 1643, 1587, 1384, 1300, 1269.

EXAMPLE 7

Acetyl RH1

Acetyl RH1 (2-Acetoxymethyl-3,6-diaziridinyl-5-methyl-1,4-benzoquinone) was synthesized according the following method. To a stirred solution of RH1 (40 mg, 0.17 mmol) in pyridine (2 mls) was added acetic anhydride (200 μl, 216 mg, 2.1 mmol). After seven hours the reaction mixture was poured into water (20 mls) and extracted with ether. The combined organic fractions were dried (Na$_2$SO$_4$) and the solvent removed in vacuo. The resulting solid was passed down a silica column using chloroform: methanol (24:1) as the eluent to yield a red precipitate. (32 mg, 68%, m.p. 114–5° C.); $^1$H NMR (400 MHz, CDCl$_3$): δ 5.08 (2H, s, CH$_2$), 2.41 (4H, s, Az), 2.34 (4H, s, Az), 2.09 (3H, s, CH$_3$), 2.05 (3H, s, CH$_3$); MS (EI+) m/z: 276 (M$^+$), 234, 217, 205, 149, 81; $v_{max}$ (film): 1738, 1643, 1587, 1384, 1300, 1230.

EXAMPLE 8

In Vitro Cytotoxicities

The cell lines used in this work were HT29, H460, H596, BE. These were obtained from the ATCC or from the European Collection for Animal Cell Cultures, ECACC. HT29 is a human colon cancer cell line and H460 is a human large cell lung carcinoma cell line. These two cell lines were used as they express relatively high levels of DTD. The corresponding matched cell lines, H596 (human lung carcinomas) and BE (human colon carcinoma), were chosen because the H596 and the BE lines do not have detectable DTD activity. Continuous challenge cytotoxicity studies were carried out on these cells (600 per well) in 96 well plates using the MTT method. After five days, the absorbances were read on a multiscan plate reader at 540 and 640nm. Plots were then drawn for inhibition of cell growth as a function concentration. Each compound was tested in triplicate at each concentration on at least two occasions.

TABLE 2

|  | H460 | H596 | HT-29 | BE | H596/H460 | BE/HT-29 |
|---|---|---|---|---|---|---|
| RH1 | 0.03 | 1.23 | 0.17 | 2.97 | 41 | 17.5 |
| Acetyl- | 0.12 | 0.56 | 0.64 | 3.33 | 4.7 | 5.2 |
| Benzoyl | 0.06 | 0.24 | 0.39 | 0.04 | 4 | 0.1 |

All values are in nM.

Although this invention has been described with respect to specific embodiments, it is not intended to be so limited and various modifications will become apparent to those skilled in the art. Such modifications are intended to fall within the spirit and scope of the present invention.

We claim:

1. A compound 2,5-diaziridinyl-3-(hydroxymethyl)-6-methyl-1,4-benzoquinone or an ester thereof, wherein the ester has the following molecular structure:

and wherein R is phenyl, methyl, naphthyl or a protected amino acid.

2. The compound of claim 1, wherein said compound is 2,5-diaziridinyl-3-(hydroxymethyl)-6-methyl-1,4-benzoquinone.

3. The compound of claim 1, wherein said compound is an ester of 2,5-diaziridinyl-3-(hydroxymethyl)-6-methyl-1,4-benzoquinone.

4. The compound of claim 1, wherein R is phenyl.

5. The compound of claim 1, wherein R is methyl.

6. The compound of claim 1, wherein R is naphthyl.

7. The compound of claim 1, wherein R is a protected amino acid.

8. A method of treating a patient having a tumor exhibiting DT-diaphorase activity, comprising administering to the patient an effective amount of the compound of claim 1 to reduce the tumor.

9. The method of claim 8, wherein the tumor is in a tissue selected from the group consisting of lung, liver colon, breast, stomach, bladder, skin and the central nervous system.

10. The method of claim 9, wherein the tumor is a non-small cell lung carcinoma.

11. The method of claim 9, wherein the tumor is a melanoma.

12. The method of claim 8, wherein the compound is 2,5-diaziridinyl-3-(hydroxymethyl)-6-methyl-1,4-benzoquinone.

13. The method of claim 8, wherein the compound is an ester of 2,5-diaziridinyl-3-(hydroxymethyl)-6-methyl-1,4-benzoquinone.

* * * * *